US00PP17464P3

(12) United States Plant Patent
Herrington et al.

(10) Patent No.: US PP17,464 P3
(45) Date of Patent: Mar. 6, 2007

(54) STRAWBERRY PLANT NAMED 'DPI RUBYGEM'

(50) Latin Name: *Fragaria×ananassa*
Varietal Denomination: DPI Rubygem

(75) Inventors: Mark E. Herrington, Woombye (AU); Jennifer A. Moisander, Beenleigh (AU); Craig Chandler, Tampa, FL (US)

(73) Assignees: State of Queensland Through Its Department of Primary Industries and Fisheries, Brisbane (AU); Horticulture Australia Limited, Sydney (AU)

( * ) Notice: Subject to any disclaimer, the term of this patent is extended or adjusted under 35 U.S.C. 154(b) by 119 days.

(21) Appl. No.: 11/007,190

(22) Filed: Dec. 9, 2004

(65) Prior Publication Data

US 2005/0138703 P1 Jun. 23, 2005

(51) Int. Cl.
*A01H 5/00* (2006.01)

(52) U.S. Cl. ..... Plt./208

(58) Field of Classification Search ..... Plt./208, Plt./209

See application file for complete search history.

*Primary Examiner*—Kent Bell
(74) *Attorney, Agent, or Firm*—Buchanan Ingersoll & Rooney PC

(57) ABSTRACT

A new and distinct short-day strawberry cultivar is provided. Attractive medium-sized generally conical to cordiform and short wedge-shaped fruit is formed in good yields. The fruit flesh is firm, sweet and flavorful. The fruit is glossy bright red on the outside and medium red on the inside. Resistance to Fusarium Wilt is displayed. The fruiting pattern and yield are similar to the 'Sweet Charlie' (U.S. Plant Pat. No. 8,729) and 'Strawberry Festival' (U.S. Plant Pat. No. 14,739) cultivars and earlier than the 'Camarosa' cultivar (U.S. Plant Pat. No. 8,708). A highly flavorable fruit Brix/Acid balance is displayed.

6 Drawing Sheets

Botanical/commercial classification: *Fragaria×ananassa* Duchesne/Strawberry plant.
Variety denomination: 'DPI Rubygem'.

SUMMARY OF THE INVENTION

The new and distinct short-day strawberry cultivar of the present invention was the product of a controlled breeding program carried out at Nambour, Queensland, Australia (27° S., 153° E.). The seed was produced at Dover, Fla., U.S.A. The seed parent (i.e., the female parent) was the 'Earlibrite' cultivar (U.S. Plant Pat. No. 13,061), and the pollen parent i.e., the male parent) was the 'Carlsbad' cultivar (U.S. Plant Pat. No. 8,660).

The seeds resulting from this cross were germinated at Nambour, Queensland, Australia and the resulting seedlings were transplanted to raised beds where they fruited and were subjected to detailed evaluation. During the 1999 season from among approximately 3,600 of the resulting seedlings, a seedling designated 99-194 was chosen primarily on the basis of its productivity, the superior fruit appearance, and the fruit flavor. This seedling was further advanced through plot selection trials during 2000–2003. During such trials the selection criteria included yield, yield distribution, fruit size, fruit shape, external and internal fruit color, fruit resistance to bruising and abrasion, fruit shelf life, fruit flavor, overall fruit attractiveness, tolerance to disease and rain damage, plant bush type, ease of harvest, truss type, and propensity for runner production. As a result of this evaluation, a single plant of the present invention has been selected. Such plant further has been virus indexed.

It was found that the new strawberry plant of the present invention exhibits the following combination of characteristics:

(a) is a short-day cultivar,
(b) forms attractive medium-sized generally conical to cordiform and short wedge-shaped sweet and flavorful fruit with firm flesh in good yields that is glossy red on the outside and medium red on the inside,
(c) displays a fruiting pattern and yield commonly similar to the 'Sweet Charlie' (U.S. Plant Pat. No. 8,729) and 'Strawberry Festival' (U.S. Plant Pat. No. 14,739) cultivars and earlier than the 'Camarose' cultivar (U.S. Plant Pat. No. 8,708), and
(d) displays resistance to Fusarium Wilt.

The new cultivar of the present invention can be readily distinguished from previously grown strawberry cultivars as indicated by the combination of characteristics that is specified hereafter. Hereafter, comparisons of plant characteristics with specific previously known cultivars are presented.

The new cultivar possesses characteristics that commonly are sought by commercial strawberry growers. A highly favorable fruit Brix/Acid balance is displayed which has been well received during taste evaluations to date. Accordingly, the new cultivar is a promising candidate for commercial success since it produces flavorful and attractive fruit that well retains its desirable attributes even following long-distance shipment.

The new cultivar has been asexually reproduced by use of runners and by tissue culture at Stanthorpe, Queensland, Australia. The combination of characteristics exhibited by this new plant has been found to be stable and is reliably transmitted to succeeding generations following such asexual reproduction. Accordingly, the new cultivar reproduces true to type by such asexual reproduction.

The new plant of the present invention has been named 'DPI Rubygem'.

BRIEF DESCRIPTION OF THE PHOTOGRAPHS

The accompanying photographs show, as nearly true as it is reasonably possible to make the same in color illustrations of this character, typical specimens of the new cultivar. The illustrated plants had been reproduced by the use of runners and were being grown outdoors in full sun at Cleveland (FIG. 1) and Nambour (FIGS. 2 to 6), Queensland, Australia. The plant parts of FIGS. 2 to 6 were obtained from plants of the new cultivar that were approximately 13 weeks of age following transplanting. In FIGS. 2 to 6 a 1 centimeter grid is included in the background in order to readily make possible a size determination.

DETAILED DESCRIPTION

Figure 1:
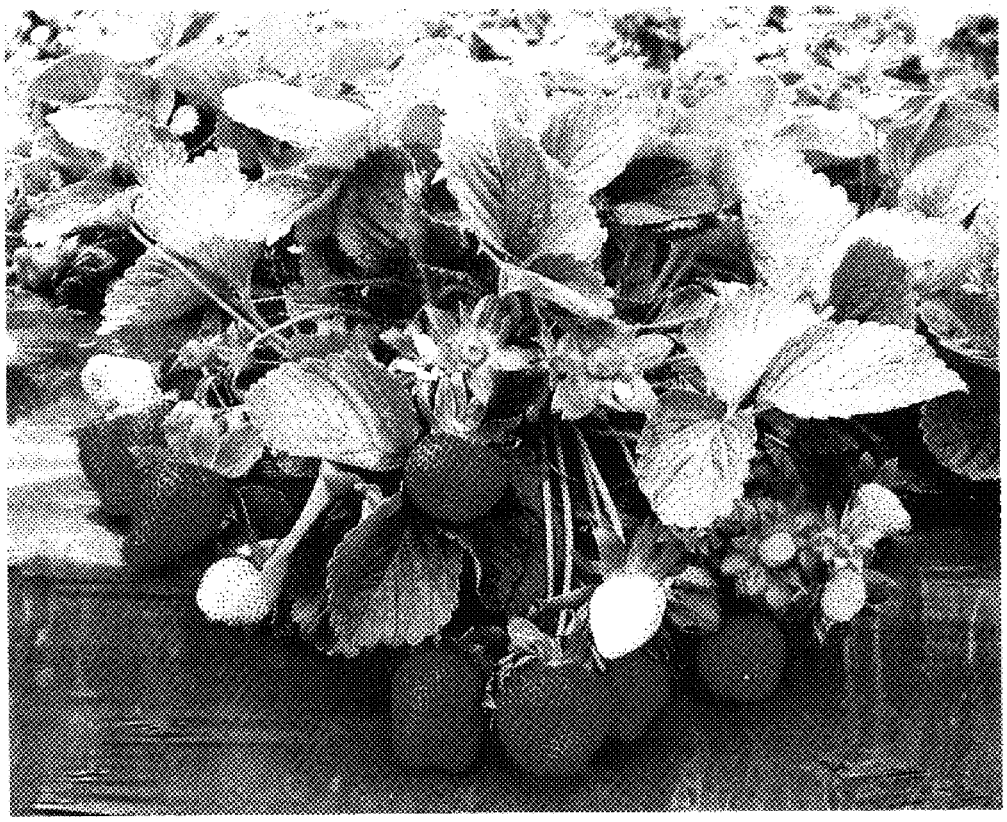
FIG. 1 illustrates typical specimen of a fruiting plant of the new cultivar. Such plant was photographed approximately 17 weeks following transplanting.

The described plants had been asexually reproduced by the use of runners, and had been planted outdoors during early April at Nambour, Queensland, Australia. The chart used in the identification of color is the R.H.S. Colour Chart of The Royal Horticultural Society, London, England (1995). Reference to common color terms is to be accorded ordinary dictionary significance.

Botanical class: *Fragaria×ananassa* Duchesne, 'DPI Ruby-gem'.

Plant:

*Type.*—Short-day.

*Configuration.*—Globose and open plant density.

*Vigor.*—Strong.

Foliage:

*Size.*—Initially the terminal leaflets are greater in length than breadth and commonly display an average length of approximately 64 mm and an average width of approximately 60 mm. In higher nutrition locations the terminal leaflets commonly display an average length of approximately 82 mm and an average width of approximately 72 mm. In the higher nutrition locations the secondary leaflets commonly display an average length of approximately 73 mm and an average width of approximately 70 mm.

*Margin.*—Commonly crenate.

Figure 2:
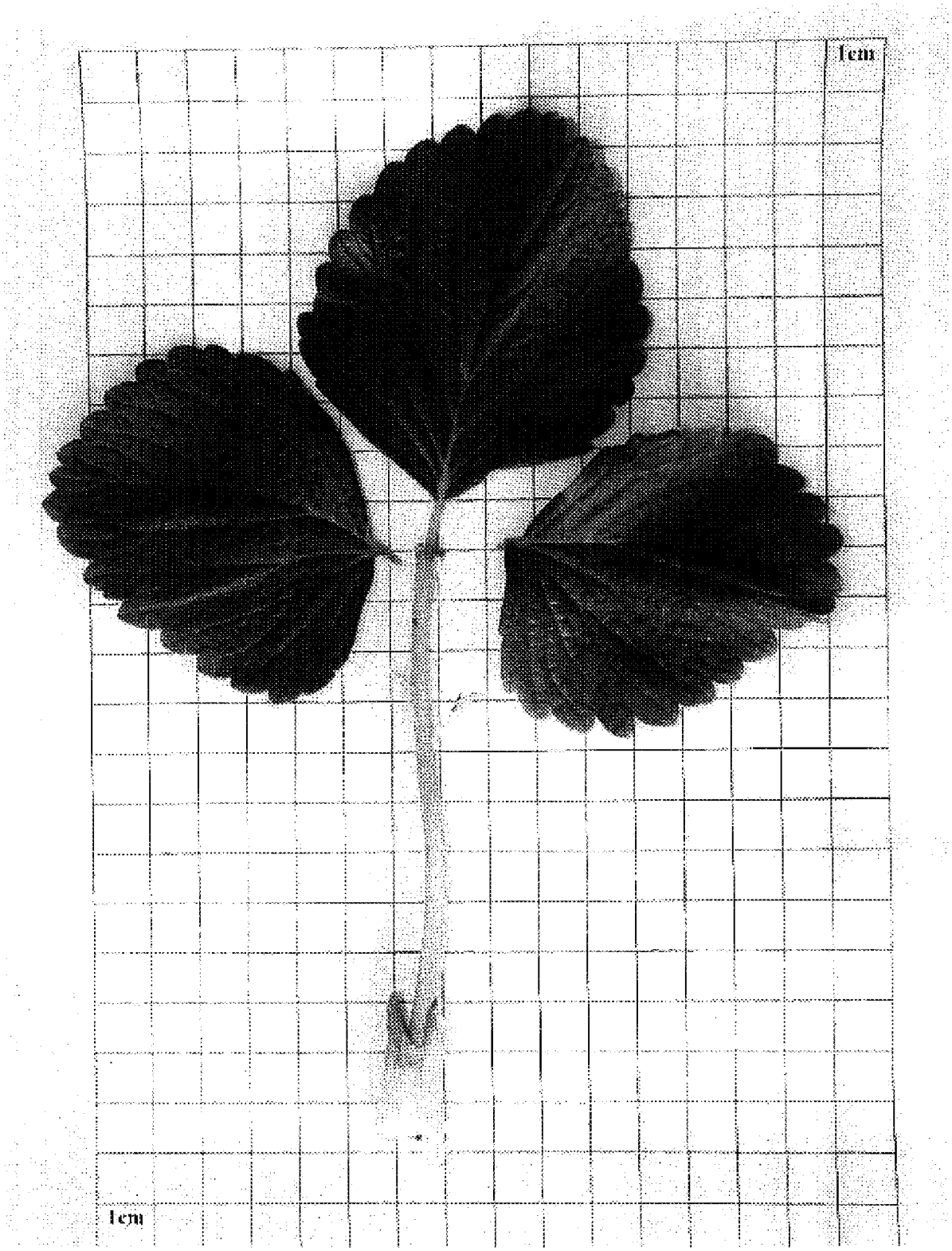
FIG. 2 illustrates typical specimens of leaves (upper surface) of the new cultivar as well as a typical stem.
Figure 3:
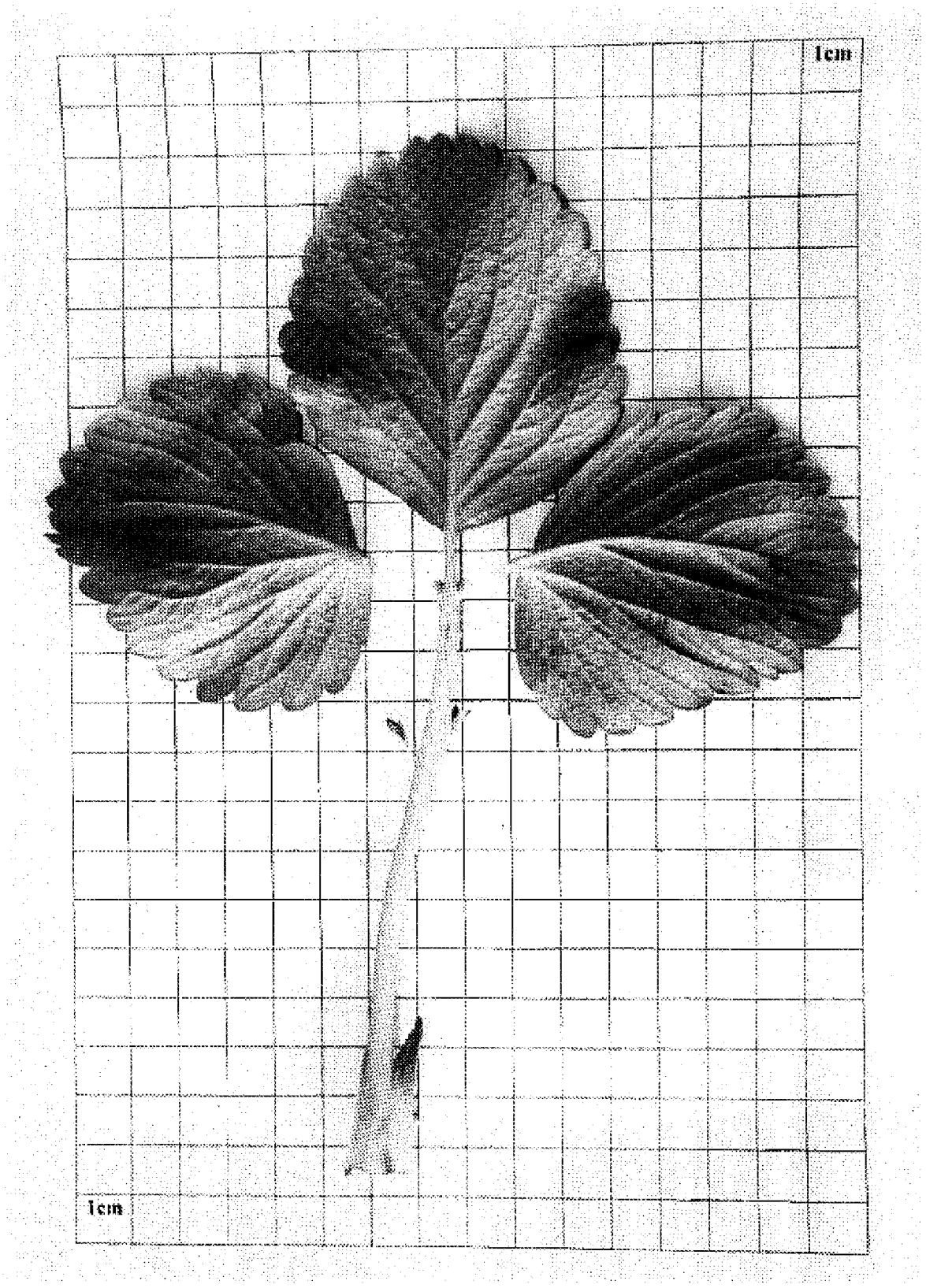
FIG. 3 illustrates typical specimens of leaves (under surface) of the new cultivar as well as a typical stem.
Figure 4:
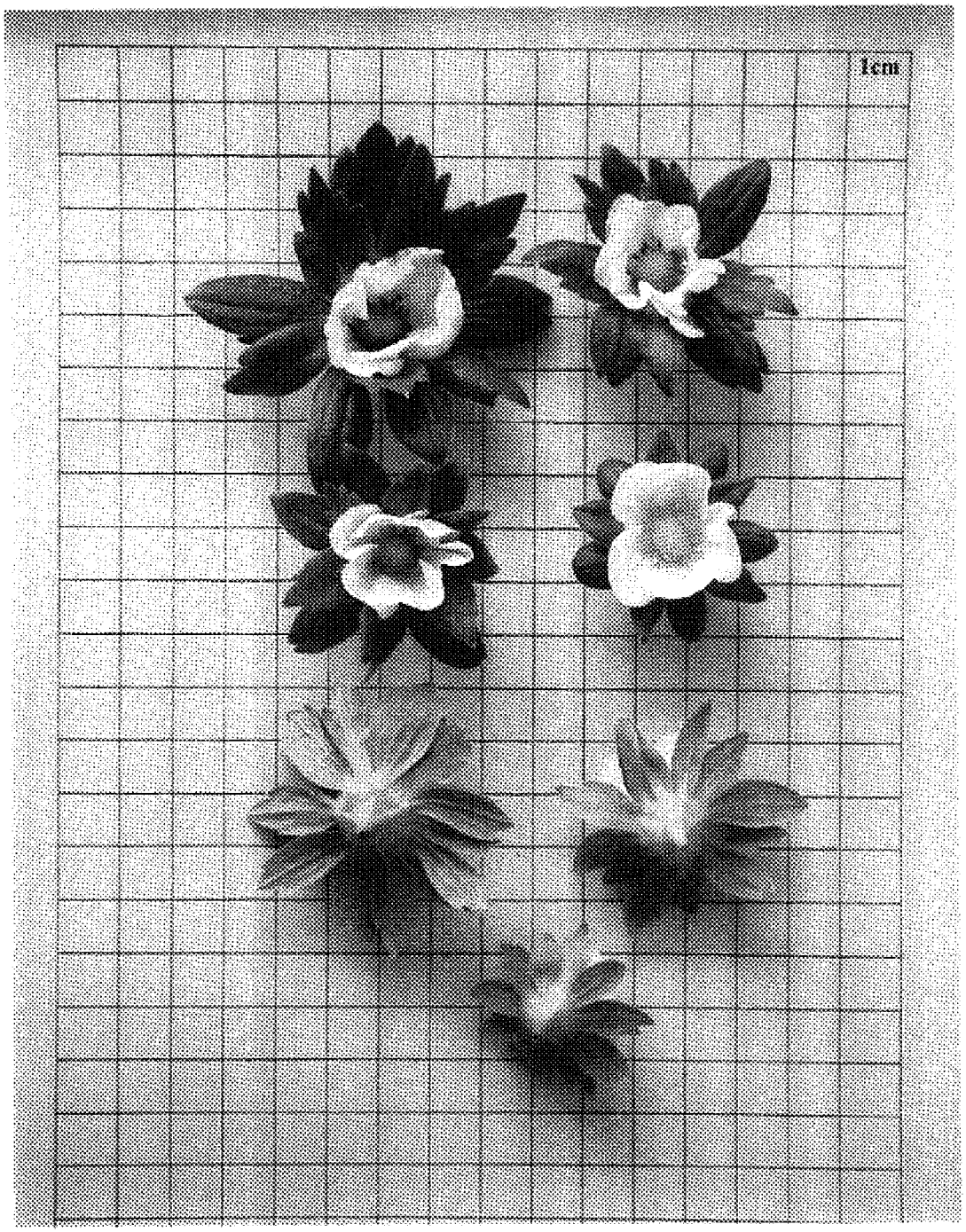
FIG. 4 illustrates typical specimens of flowers of the new cultivar with the obverse being shown at the top and the reverse being shown at the bottom.
Figure 5:
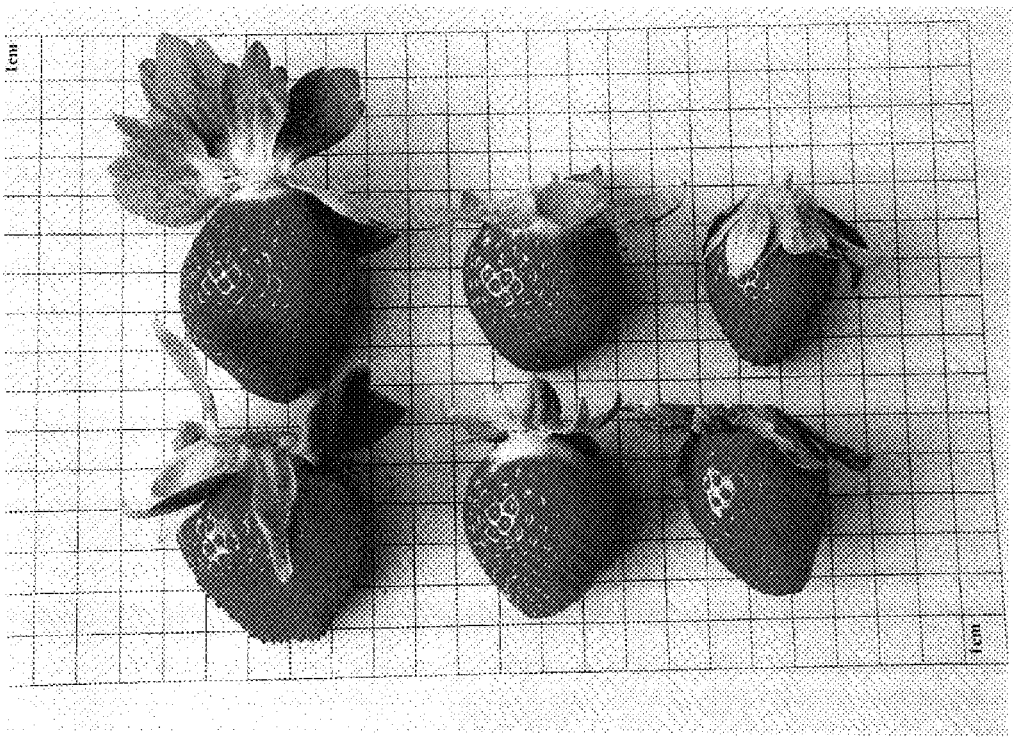
FIG. 5 illustrates externally typical specimens of the attractive medium-sized generally conical to cordiform and short wedge-shaped glossy red fruit at the new cultivar.
Figure 6:
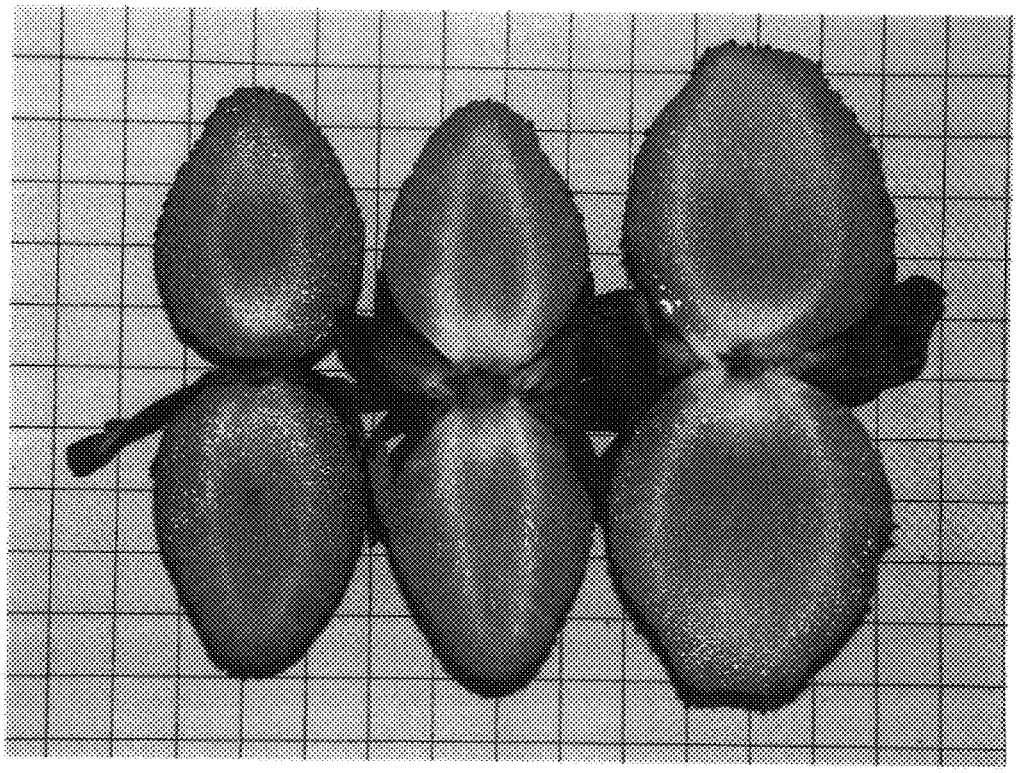
FIG. 6 illustrates internally following bisection typical specimens of the attractive juicy fruit of the new cultivar wherein the coloration generally is medium red.

*Serration.*—Approximately 21 serrations on average on terminal leaflets and approximately 20 serrations on average on secondary leaflets (as illustrated in FIGS. 2 and 3).

*Shape.*—Substantially orbicular.

*Base.*—Obtuse.

*Cross-section.*—Slightly concave.

*Blistering.*—Absent or very weak.

*Glossiness.*—Weak.

*Color.*—Upper Surface: Medium green, Green Group 137B. Under Surface: Light grey-green, Green Group 138B.

*Petiole texture.*—Medium pubescence with hairs directed strongly outwards.

*Petiole color.*—Green, Yellow-Green Group 145A.

*Stipules.*—Commonly anthocyanin coloration is absent or very weak.

*Stolons.*—Medium prescence.

Inflorescence:

*Flowering time.*—Early.

*Position.*—Approximately at canopy height.

*Size.*—Large and approximately 36.0 mm in diameter on average.

*Petals.*—Overlap, approximately 14.7 mm in length on average and approximately 14.8 mm in width on average.

*Calyx.*—Larger in size relative to the corolla.

Fruit:

*Bearing.*—Partially remontant.

*Shape.*—Generally conical to cordiform and short wedge-shaped and commonly the length is slightly greater than the width.

*Length.*—Approximately 41.6 mm on average.

*Width.*—Approximately 37.0 mm on average.

*Weight.*—Medium and commonly approximately 19 g on average, lesser than the 'Camarosa' cultivar, similar to that of the 'Strawberry Festival' cultivar, and larger than that of the 'Sweet Charlie' cultivar (See Tables 1 and 2 hereafter).

*Achenes.*—Approximately level with the fruit surface.

*Glossiness.*—Strong.

*External color.*—Red, Red Group 44A.

*Internal color.*—Medium red, Red Group 43A, and substantially evenly distributed throughout.

*Fruit center.*—Commonly solid with little hollowness, and very firm.

*Brix.*—Moderate and about the same as the 'Sweet Charlie' cultivar and higher than that of the 'Strawberry Festival' and 'Camarosa' cultivars.

*Acidity.*—Low and between that of the 'Sweet Charlie' cultivar, and the 'Strawberry Festival', and lower than the 'Camarosa' cultivar (see Table 3 hereafter).

*Calyx.*—Spreading segments, commonly much larger than fruit diameter, above the fruit, and strongly adhering.

*Fruiting.*—In replicated trials during 2003 the fruiting was approximately similar to that of the 'Sweet Charlie' and 'Strawberry Festival' cultivars and earlier than the 'Camarosa' cultivar (See Table 2).

*Yield.*—Higher early yields and equivalent total yields when compared with 'Strawberry Festival' in 2004 (See Table 1). In replicated trials during 2003 the total yield was generally comparable to the 'Sweet Charlie' and 'Camarosa' cultivars and less than that of the 'Strawberry Festival' cultivar (see Table 2).

Disease resistance: The new cultivar has been shown to be highly resistant to Fusarium Wilt (caused by *Fusarium oxysporum* Schlecht. ex Fr. f. sp. *fragariae,* Winks and Williams) during observations to date. Such resistance is similar to that of the 'Strawberry Festival' cultivar, and more resistant than that of the 'Selva' cultivar (U.S. Plant Pat. No. 5,266) (See Table 4 hereafter). The relative susceptibility to Anthracnose Fruit Rot (caused by *Colletotrichum acutatum* Simmonds), Colletotrichum Crown Rot (caused by *Colletotrichum gloeosporioides* Penz.), Angular Leaf Spot (caused by *Xanthomonas fragariae* Kennedy & King), Botrytis Fruit Rot (caused by *Botrytis cinerae* Pers. ex Fr.), Powdery Mildew (caused by *Sphaeotheca macularis* [Wallr. ex Fr.] Jacz. f. sp. *fragariae*) and to the Two-spotted Spider Mite (*Tetranychus urtricae* Koch) has not been determined since serious infestations to these have not yet been observed where appropriate control measures, such as clean planting material and predatory mite releases, have been utilized.

The following Table 1 provides yield information for plants of the 'DPI Rubygem' cultivar and the 'Strawberry Festival' cultivar for comparative purposes during 2004.

TABLE 1

| Cultivar | Mean Yield to End of May (g/plant) | Mean Yield to End of June (g/plant) | Mean Yield to End of July (g/plant) | Mean Yield to End of August (g/plant) | Mean Fruit Size (g) |
|---|---|---|---|---|---|
| 'DPI Rubygem' | 32 | 173 | 227 | 516 | 18 |
| 'Strawberry Festival' | 4 | 100 | 146 | 385 | 16 |

The following Table 2 provides typical yield information for plants of the 'DPI Rubygem' cultivar and 'Strawberry Festival', 'Camarosa', and 'Sweet Charlie' cultivars for comparative purposes during 2003.

TABLE 2

| Cultivar | Mean Yield to End of May (g/plant) | Mean Yield to End of June (g/plant) | Mean Yield to End of July (g/plant) | Mean Yield to End of August (g/plant) | Mean Fruit Size (g) |
|---|---|---|---|---|---|
| 'DPI Rubygem' | 0 | 70 | 227 | 382 | 19.4 |
| 'Strawberry Festival' | 0 | 102 | 332 | 481 | 19.4 |
| 'Camarosa' | 0 | 25 | 158 | 324 | 23.7 |
| 'Sweet Charlie' | 0 | 101 | 291 | 396 | 13.4 |

The following Table 3 provides Brix and Acid values for the mature randomly harvested fruit of the 'DPI Rubygem' cultivar and the 'Strawberry Festival', 'Camarosa' and 'Sweet Charlie' cultivars for comparative purposes. The fruit was harvested on Jul. 1 and 2, 2003, was frozen, and was assessed on Feb. 9, 2004. The Brix was a standard refractometer measure, and the Acid value was measured as titratable acidity in percent citric acid equivalents.

TABLE 3

| Cultivar | Brix | Acid |
|---|---|---|
| 'DPI Rubygem' | 9.1 | 0.60 |
| 'Camarosa' | 7.9 | 0.74 |
| 'Strawberry Festival' | 7.0 | 0.62 |
| 'Sweet Charlie' | 8.7 | 0.58 |

The fruit of the new cultivar is sweet and flavourful.

The following Table 4 provides disease reaction information with respect to Fusarium Wilt for the 'DPI Rubygem' cultivar and for the 'Strawberry Festival', 'Kabarla' (non-patented in the United States), and 'Selva' cultivars for comparative purposes. Plants were planted in contaminated soil during April 2004 and an assessment of Disease Reaction Rating was made on Nov. 17, 2004 as the percentage of plants that were dead.

TABLE 4

| Cultivar | Disease Reaction Rating |
|---|---|
| 'DPI Rubygem' | 15 |
| 'Strawberry Festival' | 18 |
| 'Kabarla' | 63 |
| 'Selva' | 15 |

Accordingly, the new cultivar of the present invention displays superior resistance to Fusarium Wilt.

What is claimed is:

1. A new and distinct strawberry plant that exhibits the following combination of characteristics:

(a) is a short-day cultivar, (b) forms a attractive medium-sized generally conical to cordiform and short wedge-shaped sweet and flavorful fruit with firm flesh in good yields that is glossy red on the outside and medium red on the inside, (c) displays a fruiting pattern and yield commonly similar to the 'Sweet Charlie' (U.S. Plant Pat. No. 8,729) and 'Strawberry Festival' (U.S. Plant Pat. No. 14,739) cultivars and earlier than the 'Camarosa' cultivar (U.S. Plant Pat. No. 8,708), and (d) displays resistance to Fusarium Wilt; substantially as illustrated and described.

* * * * *